United States Patent [19]

Cosman

[11] Patent Number: 5,233,515
[45] Date of Patent: Aug. 3, 1993

[54] REAL-TIME GRAPHIC DISPLAY OF HEAT LESIONING PARAMETERS IN A CLINICAL LESION GENERATOR SYSTEM

[76] Inventor: Eric R. Cosman, 872 Concord Ave., Belmont, Mass. 02178

[21] Appl. No.: 535,733

[22] Filed: Jun. 8, 1990

[51] Int. Cl.⁵ .................... G06F 15/42; A61N 1/00
[52] U.S. Cl. .................. 364/413.02; 128/734; 128/736
[58] Field of Search ........... 128/734, 736, 784, 785, 128/804, 660.02, 660.06; 364/413.02, 413.01, 413.06, 413.09; 606/34

[56] References Cited

U.S. PATENT DOCUMENTS 4,411,266 10/1983 Cosman .................. 128/303.18
4,805,621 2/1989 Heize et al. .............. 128/419 PG
4,907,589 3/1990 Cosman .................. 606/34

Primary Examiner—Roy N. Envall, Jr.
Assistant Examiner—A. Bodendorf

[57] ABSTRACT

A real-time graphic display of heat lesioning parameters in a clinical lesion generator is disclosed. The graphic display provides a display of heat lesioning parameters such as, impedance, temperature, power current, voltage as well as the change or alteration of various physiologic parameters such as, ECG, as a function of time during the course of the lesion process and for a time before and after the process. Benchmark values for these parameters can be set to provide visual references on the graphic display.

19 Claims, 1 Drawing Sheet

REAL-TIME GRAPHIC DISPLAY OF HEAT LESIONING PARAMETERS IN A CLINICAL LESION GENERATOR SYSTEM

BACKGROUND TO THE INVENTION

Heat lesion generators for producing clinical lesions or ablations in the human body have been commonplace for the last several decades. A particularly common type system is the radiofrequency lesion generator system exemplified by models produced by Radionics, Inc., of Burlington, Massachusetts These are power sources with a power source control and various or display readouts to monitor lesioning parameters, such as current, time, power, voltage, temperature, and impedance. The output of the lesion generator is connected to an electrode which is inserted into the body, and there is an indifferent connection to a reference electrode to complete the electrical circuit An operator would raise the power control to increase the temperature of the tip, which may be monitored, to produce the desired lesion at a given target temperature for a given time.

What has not been done heretofore is to provide real-time graphic means on a graphic display module which shows the course of the lesion as the heating proceeds. This implementation would be very helpful and useful in the neurological and cardiac fields, especially in the cardiac field where a catheter is inserted through vessels into the heart muscles area Here there are strong dynamic effects caused by the pulsation of the heart, passage of fluid, and impingement on tissue, all of which affect the impedance and can affect the course of the temperature rise during heating To be able to watch the impedance and the temperature on a graphics display would be extremely illuminating and could tell the operator at what point the lesion is satisfactorily large and when to shut off the unit or to cut back the power, Also having capabilities to watch the ECG or other electric output or potentials from the lesion tip through the lesion generator while you are making the heat lesion would give added and very important insight into the effect of the heat lesion on the target tissue Thus, an objective of the present invention is to provide in a lesion generator system an appropriate graphics display to display in real time, in color the various essential parameters for heat lesioning. In addition, an objective of the invention is to provide benchmark or set point values on the graphic display so the operator has an instant impression of the desired end point of the heating process and where the temperature, impedance, and other parameters are relative to various desired set values Yet another objective of this invention is to provide connections to monitor and display the physiologic electrical signals from the lesion electrode tip to see their change during the lesion.

SUMMARY OF THE INVENTION

A real-time graphic display of heat lesioning parameters in a clinical lesion generator provides a display of heat lesioning parameters such as, impedance, temperature, power current, voltage as well as the change or alteration of various physiological parameters such as, ECG, as a function of time during the course of the lesion process and for a time before and after the process. Predetermined values for these parameters can be set to provide visual references on the real-time graphic display.

DETAILED DESCRIPTION OF A PREFERRED EMBODIMENT

Figure 1:
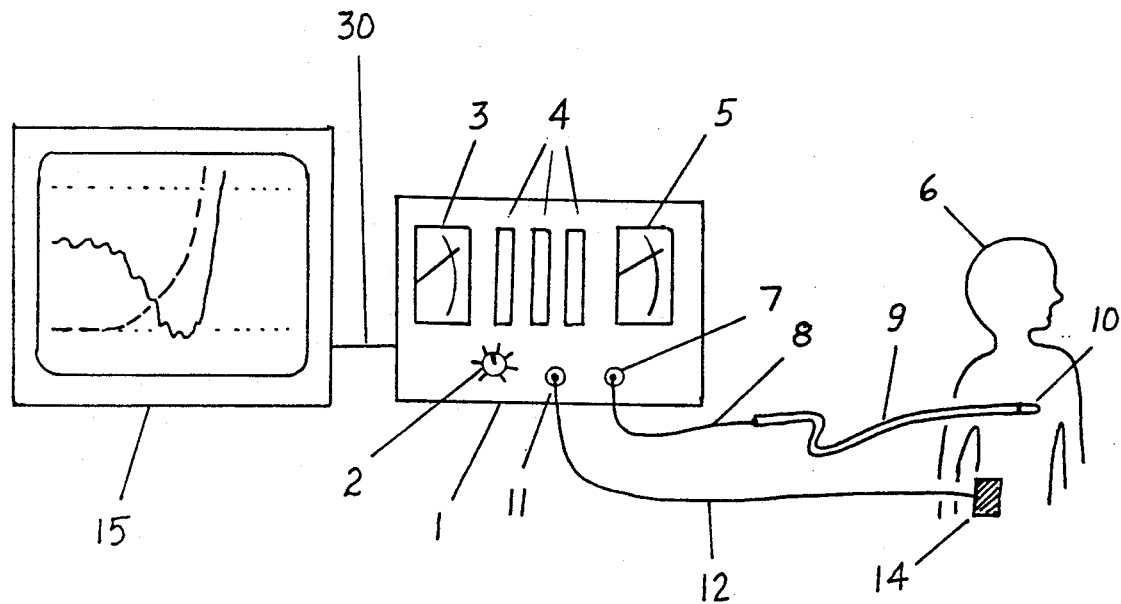
FIG. 1 shows a schematic representation of a power source generator for making a heat lesion in the body together with a module for graphics display of the lesion parameters.

In FIG. 1 is shown a lesion generator or power source 1, which is typical of existing systems. It has a power control knob 2 which enables the operator to raise the power which is delivered through the output jack 7 through cable 8 to an electrode 9 which is inserted in the body of the human patient 6 The electrode has an exposed tip 10 through which, radiofrequency, microwave or other energy sources emanate to heat the tissue near tip 10 In addition, for electromagnetic sources there typically is a reference or indifferent output jack 11 which connects through reference cable 12 to a reference area electrode 14 as a return source of current. Meter 3 display impedance while; Meters 4 display power, voltage, or current, and meter 5 displays the temperature of the tissue near tip 10. The catheter electrode, as shown in FIG. 1 , may have a thermosensor inside of tip 10 so as to monitor the heating process of the tissue surrounding the electrode. The lesion generator 1 is connected through cable 30 to a dynamic graphics monitor 15, screen. This monitor is distinguished from a simple chart recorder, which has been implemented previously on lesion generator systems.

Figure 2:
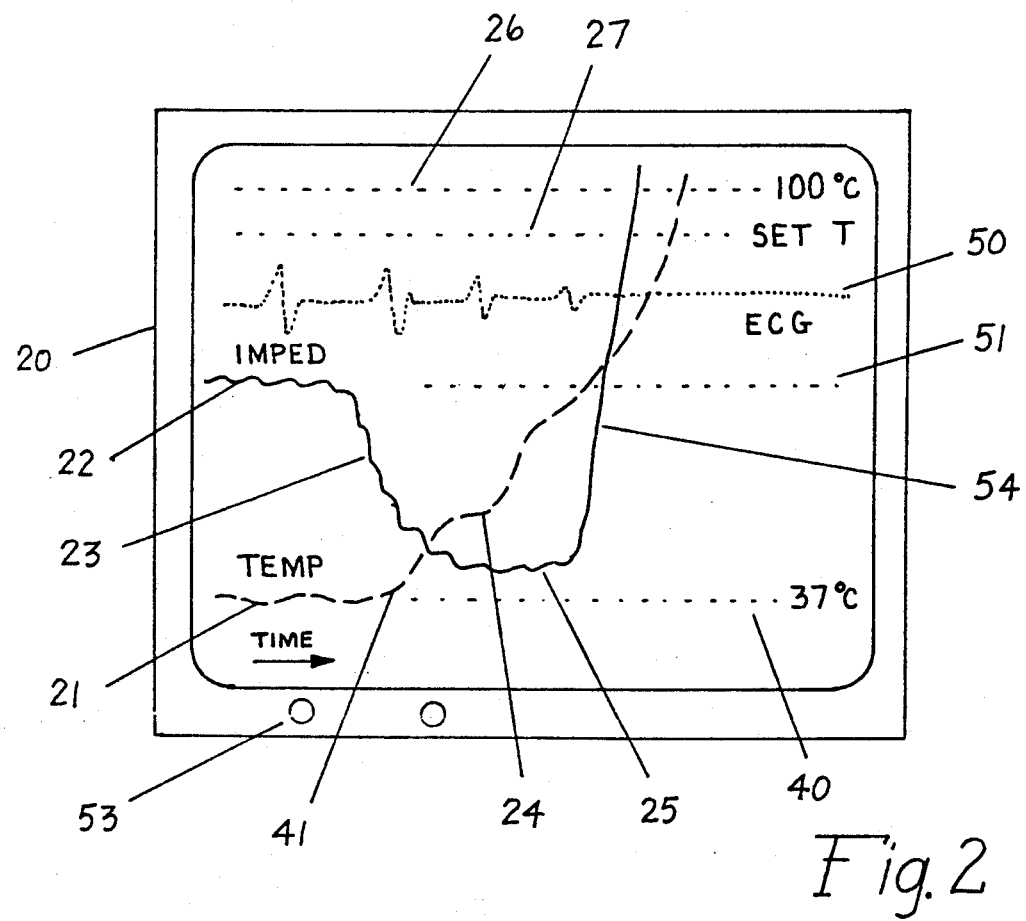
FIG. 2 shows a detailed schematic view of a graphics monitor which displays the impedance and temperature of the heat lesion process.

FIG. 2 shows more of the detail of the monitor 15. Shown on the graphics monitor is a time display of two important lesion parameters: impedance and temperature. The display monitor 20 may or may not be integrated with the lesion generator system 1 in a compact, unified cabinet Graph 21 shows the temperature curve versus time. Before lesioning begins, this curve remains at approximately 37°, which is body temperature. A dashed line 40 on the screen a representation of that important 37° benchmark temperature. Also indicated on the screen is the 100° C. line, the boiling temperature of body fluids, indicated by a horizontal, dashed line 26. When the lesion begins at the point 41, then the temperature will begin to rise In the case of cardiac ablation, this rise could be modulated by variations, as shown by the wavy portion of the dashed temperature line 24 Such variations could arise from cardiac pulsation of blood past the tip 10 or from movement of the catheter tip 10 in the heart itself Such movement could change the position of the tip 10 from regions of blood flow, to being against tissue wall, or perhaps even in or fully surrounded by the tissue wall itself. Variations of this sort would reflect themselves in more or less convection or conduction of the heat away from the tip giving rise to more or less variations in the curve 24. Cardiac pulsation of blood will also produce a cardiac related pulsation of the waveform in region 24 When the temperature approaches the 100° C. line 26, the operator must be aware that boiling and charring can occur. This is usually an undesirable effect, since it is uncontrolled and can cause enlarged damage beyond what is wished.

In addition on this graphics monitor is shown the tracing of the measured impedance, beginning with line 22. Prior to the lesion beginning, the impedance line may be reasonably steady if the electrode is stable in its position. However, some variations in impedance may be possible and related to the position of electrode tip 10. If the electrode is in the bloodstream, against tissue, or embedded in tissue, the impedance will show characteristic changes, and this will help the operator to understand the nature of the electrode's surroundings. As the heating begins, the impedance will begin to fall along curve 23. This is due to the fact that the viscosity of the ionic solution becomes less with increasing temperature At the point 25, the impedance will reach a region of a minimum value along the curve 25. Then, as the temperature approaches 100° C., the impedance will rise sharply along curve 54. This indicates to the operator that the tissue near the electrode tip is beginning to desiccate, char, and possibly boil. At that point, the operator may take action such as shutting off the lesion generator or moderating the power output.

Also shown in FIG. 2 is a real-time display of the ECG (electrocardiogram) signal 50 monitored from electrode tip 10 or from another nearby electrode. The ECG signal may change during the course of the lesion, as indicated by the attenuation of the cardiac pulse characteristic as the lesion is enlarged. This would be an indication that the lesion has had an effect on the physiology of the target tissue and thus may be a monitor of lesion progress.

The curves in FIG. 2 may be color coded, for example red for temperature, yellow for impedance, green for ECG. Additional curves for power, voltage, and current could also be displayed Having such a dynamic and visually interpretable graphic display carries more and different information than analog and digital meters which give only the instantaneous value or the instantaneous rate of change of the value of a given parameter to the operator. By having a display such as in FIG. 2, you have a real-time display which shows the history of the parameter up to the present time. In addition, you can represent on the display various set point or benchmark values indicated by the dashed temperature lines for 37° and 100° and you can also have a set point for temperature shown by line 27 and for the ambient impedance indicated by line 51, which could be pre-set by the operator just prior to making the lesion. Alternatively, one could have other set lines for the impedance at some specific value above or below the ambient impedance 51 or some percentage above or below the ambient impedance 51. This could be set by control knobs such as 53 on the panel or elsewhere programmed into the integrated monitor and lesion generator 1 and 15.

Also included in the invention is the possibility that monitor 15 or monitor 20, in FIGS. 1 and 2 respectively, could be part of a separate, stand-alone computer system into which the power unit 1 is coupled. That is to say, by using a computer with self-standing graphics and computational electronics, the signals from lesion generator 1 could be transported to the computer and then displayed in a fashion similar to that in FIG. 2. This would be a modular embodiment. Alternatively, power source monitors and displays could be built in to one console or unit, making it a unified lesioning-graphics display workstation.

It is worth noting that in the prior art physiologic parameters have been displayed on graphic means. The present invention, however, is not aimed at graphic display of physiologic parameters themselves alone but at representing graphically the parameters associated with the lesion process which is being produced specifically by the power source and the surgeon, and, as a corollary, to graphically display them simultaneously with the Physiological parameters, such as the ECG signal measured from the lesion electrode system or nearby electrodes, to see the effect on them by the lesion process. The RF lesion generator may have built-in circuitry to measure and simplify the ECG signals. It may also have appropriate filtering circuitry for this purpose to filter out the rf background or other noise. The ECG electrode may be a separate electrode, implanted on surface skin type, or it may be the same as the rf heating electrode.

The present graphics visualization technique could be applied to other heat lesioning methodologies in the body. Certainly neurological lesion generators, which have been common for many decades and which have not used this kind of visualization modality, would be an obvious objective. In addition, hyperthermia units and hypothermia units for tumor therapy would be another application.

A luminous graphics display means is advantageous here since it would enable easy visualization from a distance in a darkened room Such graphic displays have the added advantage in the operating setting, where the room lights may be darkened, that it is very easy to see the entire course history of the lesion that you are making. The character and shape of the curves have their own meaning and are visible from across the room at a glance. This is far more powerful information than merely looking at analog or digital meters on a panel which are not easy to visualize in a darkened room and have only limited time-history information. Obviously, such information could be charted out on a chart recorder as well, and the invention subsumes that possibility, but also specifically addresses the possibility of displaying such information out on a CRT, graphics console, LCD graphics display, or other display means that are available now or in the future. A CRT screen is not the only type of luminous display. Liquid crystal displays are now available that can be backlit, and there are other types of solid state displays which give a luminous appearance under the proper lighting. Projection display is another possibility. These displays distinguish themselves from a simple chart recorder since the latter is not easily seen from a distance or in poor lighting. Also distinguishing it from a chart recorder is the fact that various reference lines or set levels, as described above, can be established and displayed on the axes of the graphics screen beforehand to enable easy reference visualization for these target or set levels. It is further possible to plot these parameters not only against the time axis, but also against themselves in some other format such as a three-dimensional or isometric presentation. Several parameters can be plotted out on a multi-dimensional display which could give added clarity.

To one skilled in the art of graphics displays, there are other specific implementations of the present invention that are possible beyond the specific examples described herein, and it is the intention here to claim such other variations in this invention The claims which I wish to secure by letter patent in the U S. Pat. Office are the following:

I claim:

1. An apparatus for making and monitoring the course of a heat lesion in living bodily tissues having real-time graphics display screen monitoring of the lesion parameters, the apparatus comprising:
   (a) a controllable power source means which is adapted to be connected to an electrode that can be implanted into a living body so that the power from said controllable power source means can heat tissue near said electrode when it is implanted in the living body and with an increase in the amount of heating around said electrode producing a heat lesion in the living body;
   (b) means for measuring electrical impedance of the tissue around said electrode when it is connected to said power source means;
   (c) a real-time graphics display screen means for displaying the impedance measured by said impedance measuring means as a function o time during the course of producing the heat lesion in said living body.

2. The apparatus of claim 1 further comprising means for displaying ambient initial values of impedance on said real-time graphics display screen means.

3. The apparatus of claim 1 further comprising means for setting and displaying a predetermined value of impedance on said real-time graphics display screen means.

4. The apparatus of claim 1 wherein said electrode includes temperature sensing means, said apparatus and further comprising means for displaying an indication of the temperature sensed by said temperature sensing means in a graphics fashion on said real-time graphics display screen means.

5. The apparatus of claim 4 further comprising means graphically displaying predetermined values of temperature on said real-time graphics display screen means.

6. The apparatus of claim 5 further comprising means for setting and displaying a predetermined value of temperature on said real-time graphics display screen means.

7. The apparatus of claim 5 wherein at least some of said predetermined temperature values are 37 degrees centigrade and 100 degrees centigrade.

8. The apparatus of claim 1 further comprising means for displaying electrocardiographic signals from an ECG electrode on said real-time graphics display screen means.

9. The apparatus of claim 8 wherein said ECG electrode is the same as said implanted electrode.

10. The apparatus of claim 1 further comprising means for measuring ECG electrocardiographic signals from an ECG electrode and displaying the measured ECG signals on said real-time graphics display screen means together with said displayed measured impedance value.

11. The apparatus of claim 1 further comprising means for measuring the power from said controllable power source means and means for displaying on said real-time graphics display screen means an indication of the measured power.

12. The apparatus of claim 1 wherein said controllable power source means is a radiofrequency power source so that the heating from said electrode occurs by radiofrequency current heating in the tissue surrounding said electrode.

13. An apparatus for making heat lesions in the tissue of a living body with real-time graphics display capability of lesion parameters, said apparatus comprising:
   a controllable power source means which is adapted to deliver power to an electrode implanted in the living body with the power from said controllable power source means heating the tissue around said electrode to produce a heat lesion in the living body;
   (b) a temperature measuring means for measuring the temperature of tissue around said electrode when the electrode is heated by said controllable power source means;
   (c) a real-time graphics display screen means for displaying the temperature measured by the temperature measuring means as a function of time during the course of producing the heat lesion process.

14. The apparatus of claim 13 further comprising means for graphically displaying predetermined values of temperature on said real-time graphics display screen means.

15. The apparatus of claim 13 further comprising means for setting and displaying a predetermined value of temperature on said real-time graphics display screen means.

16. The apparatus of claim 13 wherein said controllable power source means is a radiofrequency power source so that the heating from said electrode occurs by radiofrequency current heating in the tissue surrounding said electrode.

17. The apparatus of claim 13 further comprising means for displaying electrocardiographic signals from an ECG electrode on said real-time graphics display screen means together with said displayed measured temperature value whereby the operator can observe the physiologic effect on said ECG signal .

18. The apparatus of claim 17 wherein said ECG electrode is the same as said implanted electrode.

19. The apparatus of claim 14 wherein at least some of said predetermined temperature values are 37 degrees centigrade and 100 degrees centigrade.

* * * * *